United States Patent

Samain et al.

Patent Number: 6,013,284
Date of Patent: Jan. 11, 2000

[54] SYNTHETIC PARTICULATE VECTORS AND PREPARATION PROCESS

[75] Inventors: Daniel Samain, Toulouse; Pascal Delrieu, Albi; Joëlle Gibilaro, Tours; Roselyne Dirson, Capian; Monique Cervilla, Toulouse; Ignacio De Miguel, Toulouse; Li Ding, Toulouse; Frédérique Nguyen, Vaux-Sur-Mer; Nadine Soulet, Salles-Sur-l'Hers; Corinne Soler, Canet-En-Roussillon, all of France

[73] Assignee: Biovector Therapeutics S.A., Ramonvillesainte-Agne, France

[21] Appl. No.: 08/513,853

[22] PCT Filed: Mar. 1, 1994

[86] PCT No.: PCT/FR94/00228

§ 371 Date: May 1, 1996

§ 102(e) Date: May 1, 1996

[87] PCT Pub. No.: WO94/20078

PCT Pub. Date: Sep. 15, 1994

[30] Foreign Application Priority Data

Mar. 2, 1993 [FR] France .................................. 93 02397

[51] Int. Cl.⁷ .................................................... A61K 9/16
[52] U.S. Cl. .......................... 424/490; 514/951; 514/952; 428/403; 427/2.14; 427/212
[58] Field of Search ...................................... 424/484, 498, 424/490; 514/951–52; 428/403; 427/2.14, 212

[56] References Cited

U.S. PATENT DOCUMENTS

| | | |
|---|---|---|
| 5,145,684 | 9/1992 | Liversidge et al. . |
| 5,188,837 | 2/1993 | Domb . |
| 5,607,695 | 3/1997 | Ek et al. . |
| 5,670,172 | 9/1997 | Buxton et al. . |

FOREIGN PATENT DOCUMENTS

| | | |
|---|---|---|
| 0277776 | 8/1988 | European Pat. Off. . |
| 9221329 | 12/1992 | WIPO . |

*Primary Examiner*—Edward J. Webman
*Attorney, Agent, or Firm*—Burns, Doane, Swecker & Mathis, L.L.P.

[57] ABSTRACT

A synthetic particulate vector comprising a non-liquid hydrophilic nucleus and an outer layer at least partially consisting of amphiphilic compounds, which is combined with the nucleus by hydrophobic interactions and/or ionic bonds. A process for preparing a particulate vector by encapsulating an ionizable active principle, vectors obtained according to such a process, and pharmaceutical, cosmeticological and food compositions comprising such vectors are also disclosed.

17 Claims, 3 Drawing Sheets

SYNTHETIC PARTICULATE VECTORS AND PREPARATION PROCESS

The present invention relates to new types of particles which can be used alone or as vectors for various compounds. It also relates to a process for the preparation of particulate vectors which makes possible improved control of the active principle charging.

Supramolecular biovectors or SMBVs are particles which are biomimetic of the endogenous vectors of the body and which are capable of encapsulating and of carrying a large number of active principles for, in particular, pharmaceutical, cosmetic or agribusiness use.

A first type of SMBV was described in Application EP 344,040. Their structure is very well suited to the role of vector, in particular as a result of the possibility of modifying their size and their composition according to the molecule or molecules transported and their use.

SMBVs are synthesized in three successive steps:
synthesis of a central core composed, for example, of crosslinked natural polysaccharide, which can be derived by ionic groups and brought, in particular by ultramilling, to the desired size (between 10 nanometers and a few microns, according to the desired use)
establishment of a ring of fatty acids grafted covalently solely at the periphery of the central core, in order to confer a peripheral hydrophobic nature on the latter while retaining its internal hydrophilic nature
stabilization of one or of a number of external lipid lamellae, composed in particular of phospholipids or of ceramides, sometimes with the addition of other constituents, for example of constituents of biological membranes.

The active principles, according to their physicochemical characteristics, can be transported either in the external lipid lamellae (in the case of lipophilic or amphiphilic compounds) or within the hydrophilic core (in the case of polar compounds).

Encapsulation of active principles of polar nature can take place, according to the structure of the latter, either before formation of the fatty acid ring or between this step and stabilization of the external lamella.

Despite their suitability for many uses, the synthesis of SMBVs can sometimes cause problems and in particular:
it requires a step which is problematic to control in grafting the fatty acid ring;
this grafting, carried out solely at the periphery of the core, must be carried out homogeneously, which requires in particular a prior drying step, under very specific conditions;
if the active principle is encapsulated before the grafting of the fatty acid ring, some of these molecules, localized, after their encapsulation, at the periphery of the core, can be derived by the fatty acid, leading to modification of the properties of this active principle;
if the active principle is encapsulated after the grafting of the fatty acid ring, the latter can be detrimental to the penetration of the active principle into the hydrophilic core.

The Applicant Company has shown that, surprisingly, in certain applications, it was possible to scale down the reaction scheme by not grafting the ring of fatty acids to the periphery of the crosslinked hydrophilic core.

The Applicant Company has shown that the polysaccharide particles thus obtained could be used as is. They are then named PS-type SMBVs, by analogy with supramolecular biovectors.

The Applicant Company has indeed shown that the polysaccharide particles, even of small size, could be used provided that suitable charging protocols are adopted.

They can also be used in combination with natural amphiphilic compounds, in particular phospholipids, and the Applicant Company has shown that the external lipid lamellae can possibly be arranged around this core in the absence of a grafted fatty acid ring as in the case of SMBVs. These particles have a supramolecular nature and are known as L-type SMBVs.

This is why the subject of the present invention is a synthetic particulate vector, characterized in that it comprises:
a non-liquid hydrophilic core,
an external layer composed at least in part either of amphiphilic compounds, combined with the core via hydrophobic interactions and/or ionic bonds, or by the external ring of the hydrophilic core, by using a special process which avoids encapsulation of the active principle in this ring and which concentrates the active principle in the internal part of the core.

The notion of vector must, in this instance, be understood within the broad meaning, that is to say that it comprises particles having a support role, for example when they are incorporated in a composition, either as such or for the transportation, the presentation and/or the stabilization of active compounds.

A non-liquid hydrophilic core (or matrix) can be a hydrophilic polymer. The hydrophilic matrix can in particular be composed of polysaccharides or oligosaccharides which are naturally or chemically crosslinked. The polysaccharide is preferably chosen from dextran, starch, cellulose and their derivatives.

Two types of interactions can explain the stabilization of phospholipids, for example, on a core composed of crosslinked polysaccharide which is derived throughout its bulk by ionic groups: these are either interactions of hydrophobic type or bonds of ionic type, it being possible for the two modes to collaborate in the stabilization of these lamellae.

In fact, phospholipids are composed, on the basis of a glycerol unit, of a polar head comprising a phosphate group, with a strong anionic charge, which is optionally derived by various polar groups, and of two fatty acids constituting the hydrophobic tail.

The polar head has the ability to bind itself by ionic interaction with the ionic groups grafted into the polysaccharide matrix, either via the phosphate or via the ionic groups grafted onto the phosphate of the phospholipid (quaternary ammonium phosphatidylcholines, for example).

Moreover, it is known that polysaccharides, while they have an overall hydrophilic nature, have a hydrophobic groove, which is there because the polar hydroxyl groups are directed in a given direction, allowing access to the base structure of the sugars, composed of carbon-carbon bonds, of hydrophobic nature.

In the case of polysaccharide particles constituting the core of L-type SMBVs, stabilization of compounds such as phospholipids can be due to a collaborative phenomenon between the two binding modes.

The phospholipids/polysaccharide cores combination could be demonstrated by fluorescence energy transfer techniques. The theory of energy transfer rests on the interactions which exist between two fluorophores when the emission band of the first fluorophore (F1) overlays the excitation band of the second fluorophore (F2). If the two components are close, the energy of a photon absorbed by the fluorophore F1 can be transferred to the fluorophore F2, which will then fluoresce as well as if it had been excited directly. The fluorescence of F1 can then decrease until totally extinct. The efficiency of the energy transfer between the two fluorophores is thus dependant on their spatial separation. After having labeled the polysaccharide cores using rhodamine isothiocyanate and the phospholipids using nitrobenzodiazole (NBD), an energy transfer could be demonstrated between the two fluorophores, whether in the case of L-type SMBVs of 1 μm, 200 nm or 20 nm. This transfer remains stable after incubations at 4° C., 37° C. and even at 100° C.

The hydrophilic core can be obtained by various methods and in particular, if it is a core of polysaccharide nature, by using a branched or linear biodegradable polysaccharide. This polysaccharide can be, for example, starch or one of its derivatives. Crosslinking processes are known to a person skilled in the art and can be carried out by means of bi- or trifunctional agents, such as epichlorohydrin or phosphorus oxychloride.

The properties of the polysaccharide can be modified by substituting the sugars by acidic or basic ionic functional groups which are important in the stabilization of the external lipid lamella and for the encapsulation of ionic active principles.

Encapsulation of the hydrophilic active principles can be carried out at this stage of the synthesis. The gel obtained during the synthetic step is then washed and partially dehydrated by means, for example, of centrifugation techniques, then brought into the presence of the active principle and slowly rehydrated. As the gel has the ability to swell with water, the active is carried within the polysaccharide network where it can be bound by ionic bonds with the groups grafted within the gel.

The gel obtained, whether it contains or does not contain an encapsulated compound, must be mechanically ground for the purpose of obtaining particles of desired size. The ultramilling methods are known in the state of the art and can in particular involve a high pressure extrusion using a homogenizer.

The encapsulation of hydrophilic compounds within the L-type SMBVs is generally carried out at this step. For this, the particle suspension is dried beforehand by using drying methods, such as lyophilization or atomization.

The dried particles are, for example, mixed with the active principle, which is also in the dry form. Progressive rehydration makes it possible, as in the case of the gel, to dissolve the active principle and then to carry it within the particle where it is bound by ionic bonds.

The external lipid lamella of the L-type SMBVs can be produced with various types of natural or synthetic lipids, including phospholipids and ceramides, but also ionic or nonionic surface-active agents capable of being arranged as micelles, to which other compounds, either lipid compounds or amphiphilic compounds, such as cholesterol, fatty acids or fat-soluble vitamins, can also be added.

This lamella is preferably obtained by using methods which are used for the preparation of liposomes, that is to say reversed-phase preparation, detergent dialysis or high pressure extrusion. The active principles which have to be carried or presented at the surface of the L-type SMBVs can be introduced during this step, mixed with the surface-active agents.

Another subject of the present invention is a process for the preparation of a particulate vector, characterized in that:
 a) at least one basic ionizable active principle is encapsulated in a crosslinked hydrophilic matrix grafted by acid ligands, at a pH below the $pK_a$ of the active principle,
 b) the pH of the medium is increased to a value above the $pK_a$ of the active principle,
 c) the hydrophilic matrix, containing the active principle localized mainly at the center of the said matrix, is recovered.

In fact, the adoption of a suitable protocol for the charging of hydrophilic cores makes it possible to control the topology of the charging.

The hydrophilic matrix is preferably composed of polysaccharides or of oligosaccharides, which are naturally or chemically crosslinked.

This process, which can be used with SMBVs, is more particularly important with particles in which the external lipid lamellae have been reduced (L-type SMBVs) or eliminated (PS-type SMBVs) with respect to the method described above. The Applicant Company has observed that it is difficult to use such SMBVs containing reduced lipid lamellae as vectors for the encapsulation of ionic active principles with conventional charging methods.

In fact, if molecules of the active principle are bound with the polysaccharide particle of the core while being maintained at the periphery of the core, this can result in an instability in the particle suspension, it being possible for the particles to aggregate with one another by virtue of interparticulate bonds due to the active principle. This phenomenon is relatively minor for low levels of charging of active principles, whereas it becomes very important with high levels of charging of active principles. Likewise, the size of the particles is extremely important. With particles of large size (for example greater than 100 nanometers), the ratio of the surface area to the internal volume of the particle is very low; for this reason, in comparison with the total amount of active principle encapsulated, the amount of active principle bound at the periphery of the particles is very low, thus limiting the possibilities of interparticulate bonds. In contrast, when the particles are very small in size, this aggregation phenomenon is very noticeable. It should also be noted that this phenomenon is not very marked with SMBVs which have a layer of fatty acids grafted onto the core, which then serves to isolate from interparticulate interactions.

In order to overcome this, the Applicant Company has shown that it is possible to control topologically the penetration of the active principle within the particles by controlling the ionic conditions of the encapsulation.

The polysaccharide cores can be regarded as polyelectrolyte matrices and, as such, they have a pH differential between the inside and the outside of the particle. This phenomenon is due to the more or less significant dissociation of the counterions and to the immobilization of the ionic functional groups on the polysaccharide network. This property makes it possible to control the localization of the active principle to be incorporated, by causing a solely internal encapsulation or an encapsulation solely at the surface or alternatively in the periphery of the core.

When the active principle to be incorporated is basic in nature, its solubilization in a medium with a pH below its $pK_a$ leads it to exist in the ionized form; it can then become attached to the anionic groups grafted onto the polysaccharide core. When the pH rises above the $pK_a$, the active principle is in a deionized form, which does not allow it to interact with the matrix. In order to control the localization of the encapsulated active principle, use is therefore made of the pH differential which exists between the inside and the outside of the particle: if the external medium has an excessively high pH, the active principle cannot interact with the ionic groups placed at the periphery of the cores.

The internal pH of the cores derived by acidic ligands being lower than the external pH, the active principle, which has entered the particle in the deionized form, becomes ionic again and thus is bound to the anionic groups of the L-type SMBVs. In this specific case, the active principle will be localized solely in the core of the particle, to the exclusion of the peripheral region. This type of encapsulation is thus very favorable to an optimum dispersion of the particles.

In the case of acidic active principles, it is possible symmetrically to apply the process with cores derived by basic ligands, according to the following steps:

a) at least one acidic ionizable active principle is encapsulated in a crosslinked hydrophilic matrix grafted by basic ionic ligands, at a pH above the $pK_a$ of the active principle, b) the pH of the medium is decreased to a value below the $pK_a$ of the active principle, c) the hydrophilic matrix, containing the active principle localized mainly at the center of the said matrix, is recovered.

This type of charging with topological control of the localization of the active principle in the polysaccharide core is particularly advantageous for vectorization applications with SMBVs in which the external lipid lamellae have been reduced (L-type SMBVs) or eliminated (PS-type SMBVs) but it is also suitable and desirable for SMBVs already described in the above patents, in order to increase the degree of charging or to minimize the disturbances caused to the structure of the external phospholipid lamella in the case of external attachment of macromolecules, for example of recognition units and in particular of an apoprotein.

Another subject of the invention is a particulate vector composed of a crosslinked hydrophilic core grafted by ionic groups and here called PS-type SMBV. The ionic groups can be anionic groups, such as for example phosphates, succinates or carboxymethylates, or cationic groups, for example quaternary ammoniums or amines. The size of the PS-type SMBVs is preferably between 20 nm and 200 nm.

The crosslinked hydrophilic core can be composed of natural or synthetic polymers which are naturally or chemically crosslinked. Use is in particular made of polysaccharides or oligosaccharides, such as starch, dextran, cellulose and their derivatives.

Advantageously, an active principle is encapsulated in the PS-type SMBV mainly at the center of the matrix; the external part of the core is virtually devoid of active principle, which makes it possible to avoid the aggregation phenomena which generally occur for particles of small size.

One of the subjects of the invention is therefore a particulate vector composed of a crosslinked polysaccharide matrix containing an active principle, the said active principle preferably being localized mainly at the center of the matrix.

According to yet another aspect, a subject of the invention is a process for charging which makes it possible to encapsulate the active principle in a complete SMBV, a PS-type SMBV or an L-type SMBV, which can be in the form of a suspension.

The charging is carried out on the particulate vector on which the various lipid and/or amphiphilic layers are, if appropriate, fixed. In order to do this, the hydrophilic core must contain ionic groups. The process thus requires the following steps:

a) a crosslinked hydrophilic core is prepared in which ionic groups are fixed, b) optionally, lipid compounds, such as, for example, fatty acids, are fixed on the crosslinked core and/or an amphiphilic lamella (a phospholipid lamella, for example) is formed on the core which is optionally acylated, c) the active principle is charged within the vector at a pH suitable for the active principle and while supplying energy, d) having incorporated the active principle, the vector is recovered.

In the case of PS-type SMBVs, it is difficult to use conventional charging methods for incorporating ionic active principles. It is true that methods with topological control make it possible to overcome this problem. However, topological control requires precise adjustment of the pH which must be compatible with the active principle and the vector.

In the case of normal or of L-type SMBVs, the methods developed until now comprise incorporation of the active principle in the cores and the subsequent formation of the phospholipid lamella. These methods certainly produce very advantageous incorporation results but require the active principle to be handled at all steps of the preparation process. In the case of very toxic or very expensive active principles, these methods cannot be recommended for reasons of safety or of cost.

The Applicant Company has therefore developed an alternative method to overcome these problems. The ionic ligands grafted into the polysaccharide network of the vectors result in a significant affinity for the ionic active principles of opposite charge. However, this affinity, during the incorporation, must be controlled in order to avoid aggregation of the vectors and to make it possible to localize the active principle mainly within the particles. For the precharging, this control requires precise adjustment of the pH or a low level of incorporation. This aggregation is mostly due to localization of the active principle at the surface, which localization is itself due to the presence of ligands at the surface of the particles.

In order to effect this new type of charging, three factors come into play:

a) a significant affinity of the active principle for the vector in order to provide for incorporation of the active principle: this affinity is created by acidic or basic ionic ligands which are grafted into the crosslinked polymer; the density and the strength of the ligands can be adjusted according to the active principle, b) a significant dispersion of the vectors during the incorporation in order to avoid the interactions between particles which promote aggregation: this dispersion can be provided for by the dilution of the vectors in the reaction medium at a concentration which is sufficient to decrease the interparticulate interactions but also at a concentration which is compatible with pharmaceutical applications, c) the use of any means for promoting entry of the active principle within the vector: the contribution of energy, in the form, for example, of stirring or of heat, will accelerate the kinetics of entry of the active principle but will also promote dispersion of the vectors; the appropriate form of the active principle, which must be sufficiently ionic to make it possible to attach the active principle but also the least charged, in order to avoid surface interactions.

For SMBVs or L-type or PS-type SMBVs, it is possible to use incorporation protocols corresponding to these requirements. The presence of grafted ionic ligands in the crosslinked polymer provides for attachment of the active principles for the three species. Dispersion of the vectors can be carried out by suspending PS-type SMBVs in water. SMBVs or L-type SMBVs are prepared from acylated or polysaccharide cores and from phospholipids dispersed beforehand in aqueous medium and are thus suspended in water. The contribution of energy, for example in the form of stirring or of heat, does not damage the SMBVs. It is possible to vary the pHs and to define pH ranges which are compatible with this type of charging.

In the case of SMBVs and of L-type SMBVs, the lipid and/or phospholipid lamellae represent a barrier which must be crossed by the active principles. However, in the charging process described, two additional factors intervene to promote this crossing:
 a) the contribution of energy which can fluidify the lipid and phospholipid lamellae and increase the kinetics of entry of the active principle within the vectors,
 b) the form of the active principle which can be very weakly ionic due to the existence of the gradient existing between the interior and the exterior of the vector.

In addition, the strong affinity between the active principle and the crosslinked polyelectrolyte polymer provides for its attachment and the strong dispersion prevents aggregation of the vectors with one another.

This new process makes it possible to prepare SMBVs of any type which are charged with active principle, while retaining the size of the base vectors, and has many advantages. This method consists in preparing the blank vectors, without active principle, before the incorporation, which makes it possible to process the blank vectors, according to conditions which are suitable for the vectors and which do not depend on the active principle to be encapsulated, and subsequently to charge. These conditions can therefore be more or less drastic. They also make it possible to be able to characterize the blank vector as base entity.

The incorporation step is the final step of the process, which results in the active principle, which is capable of being toxic and expensive, being handled during only one step of the process. This process thus reduces the handlings and the possible losses of the active principle. It therefore makes it possible to be more certain as regards safety but also more profitable.

In addition, for some active principles, the incorporation conditions can be relatively simple, which makes it possible to envisage charging the vectors with the active principle at the time of use. This method of preparation at the time of use can eliminate the problems of storage in the liquid state.

This new method of charging is based on the significant affinity between the vectors and the ionic active principles but also on the simple control of the incorporation by the dispersion of the vectors and the ionic form of the active principle. It has very worthwhile advantages: preparation of the blank vector independent of the active principle, handling of the active principle in a single step and the possibility of preparation at the time of use.

Another subject of the invention is a particulate vector which contains, from the inside towards the outside, a crosslinked polysaccharide matrix containing an ionizable active principle, a first lipid layer fixed to the matrix by covalent bonds and a second layer of amphiphilic compounds on which protein or peptide molecules are optionally grafted.

The particulate vectors according to the invention preferably have a diameter of between 10 nm and 5 μm and more preferably between 20 and 70 nm.

These particulate vectors are intended to carry or to present at their surface one or a number of molecules possessing biological activity. Mention must be made, among these molecules, without this list being limiting, of:
 antibiotics and antivirals,
 proteins, proteoglycans, peptides,
 polysaccharides, lipopolysaccharides,
 antibodies,
 antigens,
 insecticides and fungicides,
 compounds which act on the cardiovascular system,
 anticancers,
 antimalarials,
 antiasthmatics,
 compounds having an effect on the skin,
 constituents of dairy fat globules.

In the examples below, a description will be given of the charging of various products according to their characteristics, and in particular:
 a hydrophilic product of small size intended for systemic administration,
 of an active principle possessing anticancer activity,
 of two enzymes possessing antibacterial activity, lactoperoxidase and glucose oxidase,
 of a plant extract composed of procyanidol oligomers possessing an antioxidant activity,
 of constituents of the fat globule of milk.

Just like SMBVs having a ring of grafted fatty acids, L-type SMBVs can be sterilized either by filtration or by autoclaving. They can also be frozen or lyophilized, for example in the presence of an additive, or alternatively atomized.

The advantages of L-type or of PS-type SMBVs are in particular:
 a modular construction which allows adaptation to the product to be carried or to be presented
 a biomimicry with respect to natural structures, such as lipoproteins or dairy fat globules
 a greater ease of synthesis and of industrialization with respect to SMBVs containing a fatty acid ring
 great chemical and thermal stability due to the polymeric structure of the core
 a defined size and the possibility of homogeneously obtaining very small sizes (20 nm)
 their ability to stabilize the compounds encapsulated within the core and in particular enzymes or antioxidant compounds.

The subject of the invention is therefore a pharmaceutical composition, characterized in that it contains a particulate vector according to the invention and a pharmaceutically acceptable support for its administration. The vectors according to the invention are in particular useful for therapeutic and immunological applications.

Another subject of the invention is a cosmetological composition, characterized in that it contains a particulate vector as described above and cosmetologically acceptable excipients.

Finally, food compositions containing particulate vectors according to the invention form parts of the invention.

The examples which follow are intended to illustrate the invention without limiting the scope thereof.

BRIEF DESCRIPTION OF THE DRAWINGS

In these examples, reference will be made to the following figures.

EXAMPLE 1

Figure 1:
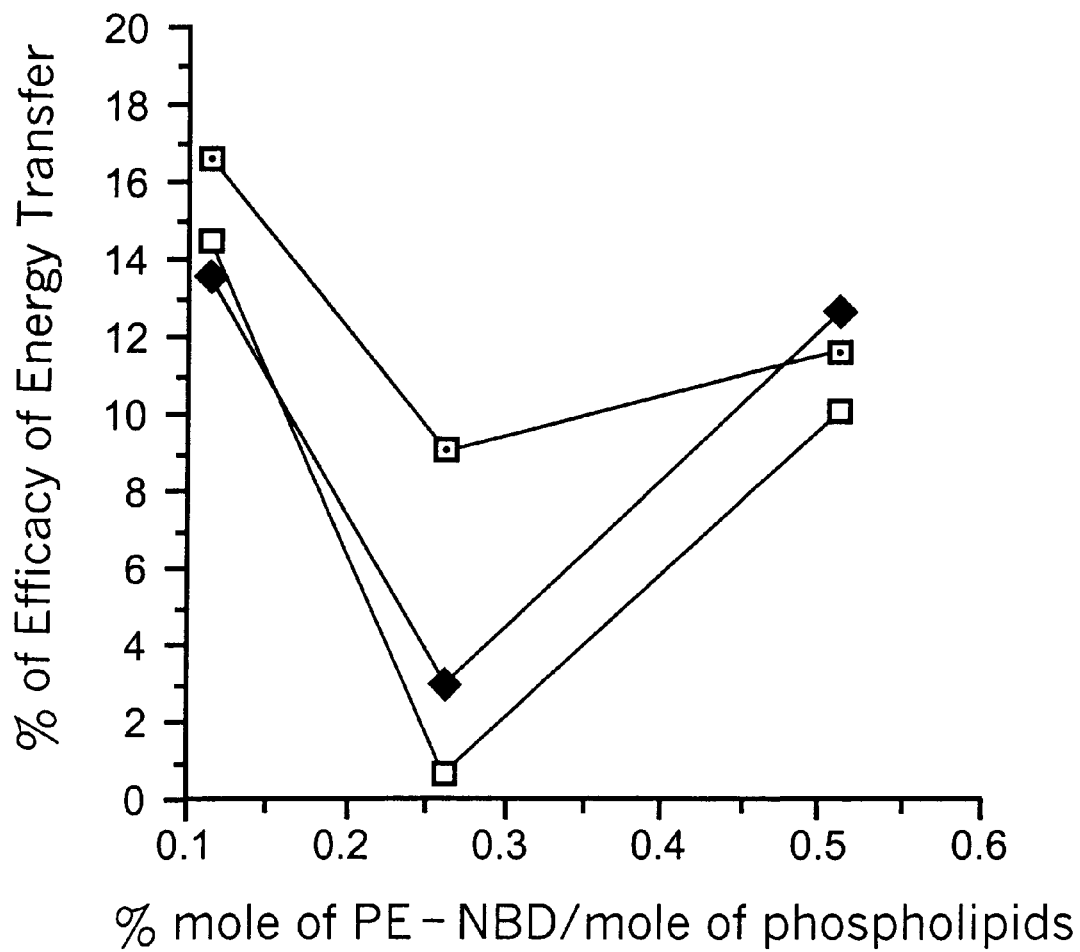
FIG. 1 Energy transfer on L-type SMBVs labeled with two types of fluorescent ligands. The polysaccharide core is labeled using rhodamine and the phospholipid layer is labeled using NBD.

Preparation of Polysaccharide Particles with a Mean Diameter of 20 Nanometers, by Twofold Crosslinking of Dextrin by Phosphorus Oxychloride 100 g of dextrin (Roquette) are introduced into a 3 liter jacketed reactor and are dissolved in 350 ml of demineralized water and 100 ml of 10N sodium hydroxide.

After homogenization, 35.3 ml of POC13 and 225 ml of 10N sodium hydroxide are added simultaneously.

After the end of the addition of the reactants, the reaction mixture is stirred for a further 15 minutes and then neutralized by addition of hydrochloric acid.

The gel is diluted in 2 liters of demineralized water and homogenized at 900 bars using a high pressure homogenizer (Westfalia). This step makes it possible to obtain matrices with a mean diameter of 20 nm.

The matrices are then washed by precipitation with ethanol in order to remove the salts and then dried by lyophilization at a concentration of 30 g/l of matrices and 20 g/l of ammonium bicarbonate.

75 g of lyophilized matrices are recovered (reaction yield 75%).

EXAMPLE 2

Preparation of Polysaccharide Matrices Grafted by Cationic Quaternary Ammonium Groups 200 grams of amylopectin (Roquette, Lille, Fr.) are dispersed in 500 milliliters of 2N sodium hydroxide in a 5 liter reactor. When the solution is well homogenized, 93.6 grams of glycidyltrimethylammonium chloride (Fluka, CH), corresponding to 0.5 equivalents/glucose residue, dissolved in 150 milliliters of water, and 11.4 grams (i.e. 9.7 milliliters) of epichloroydrin (Fluka, CH), corresponding to 0.1 equivalents/glucose residue, are simultaneously introduced. The mixture is homogenized for 1 to 2 hours and then left standing for 8 hours. The polymerized starch preparation is then brought to pH 6 by addition of acetic acid. The gel obtained is then washed a number of times with distilled water until all the salts and reaction by-products have been removed.

After lyophilization, 244 grams of crosslinked gel are obtained, i.e. a reaction yield of 80%.

EXAMPLE 3

Preparation of Polysaccharide Matrices Grafted by Anionic Groups of Carboxymethyl Type ("CM-Type")

200 grams of dextrin (Roquette) are dissolved in 300 milliliters of 7N sodium hydroxide in a 5 liter reactor. When the solution is well homogenized, 9.6 milliliters of epichloroydrin (Fluka, CH), corresponding to 0.1 equivalents/ glucose residue, and 117.2 grams of chloroacetic acid, dissolved in 80 milliliters of water, are simultaneously introduced.

After stirring for 1 hour, 9.6 milliliters of epichlorohydrin and 150 milliliters of 20N sodium hydroxide are added while stirring vigorously. After the end of the addition, the preparation is homogenized for 6 hours and then left standing overnight. The gel thus obtained is suspended in 1 liter of water and acidified to pH 3–4 by addition of 2N hydrochloric acid. The gel is then filtered and washed with distilled water. After lyophilization, 276 grams of gel of carboxymethyl type are obtained, i.e. a yield greater than 80%.

EXAMPLE 4

Preparation of Hydrophilic Matrices, with a Mean Diameter of 1 $\mu$m, by Crosslinking of Starch by Phosphorus Oxychloride 100 g of wheat starch (Roquette) are introduced into a 3 liter jacketed reactor and dissolved in 375 ml of distilled water and 100 ml of 10N sodium hydroxide.

The mixture is stirred for 15 minutes at room temperature.

Once the mixture is homogenized, 11 ml of $POCl_3$ and 50 ml of 10N sodium hydroxide are simultaneously added. After the end of the addition of the reactants, the reaction mixture is stirred for a further 15 minutes and then neutralized to pH 7 by addition of acetic acid.

The gel is washed in a centrifuge (Rousselet) for 30 minutes with distilled water so as to remove the excess salts and reaction by-products.

The gel thus obtained is then homogenized at high pressure (500 bars, Westfalia minilab homogenizer). This step makes it possible to obtain matrices with a mean size of 1 $\mu$m. The titration of 1 g of crosslinked gel using an automatic titrimeter (Methrom 682 titro-processor) reveals a degree of crosslinking of 0.3 meq of phosphodiester functional groups per gram of crosslinked gel.

PS-type SMBVs with a diameter of 1 $\mu$m are thus obtained.

EXAMPLE 5

Production of Ionic Polysaccraride Particles of 200 Nanometers 15 grams of gel obtained according to Example 2, or of CM-type gel obtained according to Example 3, are dispersed in 500 milliliters of distilled water and homogenized by means of a Rannie MiniLab 12–51 homogenizer (APV Rannie, Copenhagen, Dk). The homogenization pressure applied is 600 bars for 12 minutes.

A fluid suspension of basic or acidic crosslinked polysaccharide particles is obtained, the size of the particles, measured with a Coulter N4MD Nanosizer, being centered around 200 nanometers. The nanoparticles are then dried by lyophilization in the presence of 20 grams/liter of ammonium bicarbonate.

PS-type SMBVs with a diameter of 200 nm are thus obtained, which can be used as is or converted to L-type SMBVs.

EXAMPLE 6

Preparation of L-Type SMBVs from Particles of 20 Nanometers

Preparation of blank L-type SMBVs 10 mg of 20-nm polysaccharide cores are dispersed in 2 ml of 50 mM octyl glucopyranoside OGP (Fluka). They are mixed under ultrasound with a solution of 10 mg of an 80/20 mixture of purified egg yolk lecithins (Sigma) and of cholesterol (Sigma) dispersed in 2 ml of 50 mM OGP. This preparation is then suddenly diluted under ultrasound to a final OGP molarity of 5 mM and then dialyzed extensively for 48 hours. Analysis of the size is carried out using a Coulter N4 nanosizer indicates that 97% of the particles have a diameter of 23 nm.

EXAMPLE 7

Characterization by Energy Transfer on L-Type SMBVs of 20 Nanometers

A—Preparation of L-type SMBVs labeled by fluorescence
 a—Preparation of polysaccharide cores labeled with rhodamine (λ ex540 nm—λ ex580 nm)

50 mg of 20-nm polysaccharide cores, prepared according to Example 6, are dispersed in 1 ml of 100 mM, pH 10, sodium bicarbonate (Sigma). 0.5 mg of rhodamine B isothiocyanate (Sigma), dissolved in dimethyl formamide (SDS), is added, i.e. 1% of rhodamine with respect to the weight of polysaccharide cores. After stirring for 18 hours at room temperature, a number of washings with ethanol are carried out in order to remove the unreacted rhodamine. The cores are then dried by lyophilization.

b—Formation of the phospholipid lamella labeled with nitrobenzodiazole (NBD)
(λ ex470 nm—λ ex530 nm)
* From fluorescent polysaccharide cores 10 mg of cores of 20 nm labeled using rhodamine isothiocyanate are dispersed in the presence of 2 ml of 50 mM octyl glucopyranoside OPG (Fluka). 10 mg of a 79/20/1 mixture of purified egg yolk lecithins (Sigma), of cholesterol (Sigma) and of phosphatidylethanolamine labeled with nitrobenzodiazole NBD (Sigma), dispersed in 2 ml of 50 mM OGP, are then introduced into the suspension, i.e. 100% of phospholipid mixture with respect to the polysaccharide cores. This solution is then suddenly diluted to a final OGP molarity of 5 mM under ultrasound and then dialyzed extensively for 48 hours.

* From non-fluorescent polysaccharide cores

The L-type SMBVs are prepared in an identical way but with non-fluorescent polysaccharide cores. This preparation is used as control, it represents the zero level of the energy transfer.

B—Preparation of control fluorescent polysaccharide cores: PS-type SMBVs 10 mg of 20-nm fluorescent cores are dispersed in the presence of 2 ml of 50 mM OGP. This solution is then suddenly diluted to a final OGP molarity of 5 mM under ultrasound and then dialyzed extensively for 48 hours.

C—Preparation of control fluorescent liposomes 10 mg of the above phospholipid mixture are dispersed in 2 ml of 50 mM OGP. The solution is suddenly diluted to a final OGP molarity of 5 mM under ultrasound and then dialyzed extensively for 48 hours.

D—Preparation of control SMBVs

SMBVs labeled with two types of fluorescent ligands (acylated core labeled using rhodamine and phospholipids labeled using NBD) as well as SMBVs possessing non-fluorescent acylated cores and the phospholipid layer labeled using NBD were prepared according to the methods described in the above patents (EP 344,040).

The energy transfer is quantified by the decrease in the fluorescence of the NBD (emission wavelength at 530 nm). A fluorescence energy transfer of 20% was demonstrated on the L-type SMBVs labeled with two types of fluorescent ligands with respect to the L-type SMBV in which only the phospholipid layer has been fluorescently labeled (FIG. 1). This transfer remains stable after incubating for 4 hours at 4° C. and at 37° C., as well as after incubating for 2 hours at 100° C. This clearly tends to demonstrate that the phospholipids and the polysaccharide cores are close in space. The intimate phospholipid/polysaccharide cores combination is confirmed. Simple mixing of the control fluorescent polysaccharide cores (PS-type SMBV) with control fluorescent liposomes does not lead to energy transfer between the two fluorophores, even under the above incubation conditions.

Figure 3:
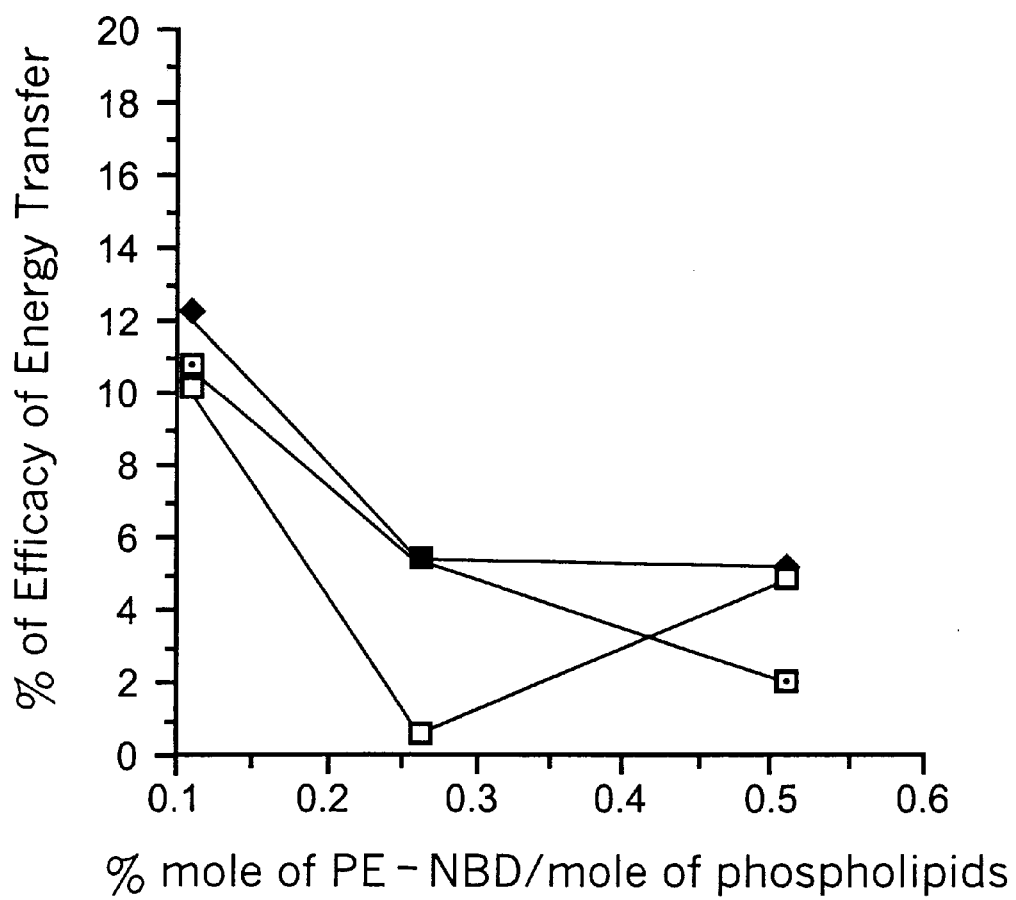
FIG. 3 Energy transfer on SMBVs labeled with two types of fluorescent ligands. The acylated core is labeled using rhodamine and the phospholipid layer is labeled using NBD.

The energy transfer observed on L-type SMBVs is comparable with the energy transfers observed on SMBVs under the same experimental conditions (FIG. 3).

EXAMPLE 8

Preparation of L-Type SMBV from Polysaccharide Particles of 200 Nanometers 10 grams of PS-type SMBV, prepared according to Example 5, are dispersed in 500 milliliters of distilled water and placed in a Rannie Mini Lab 12-51 homogenizer (APV Rannie, Copenhagen), under a pressure of 300 bars, at a flow rate of 10 liters/hour. 0.5 grams of hydrogenated soya phosphatidylcholine (Nattermann, Fr.) are injected directly into the suspension which is recirculating in the homogenizer. This preparation is homogenized for 12 minutes.

The suspension obtained contains dispersed L-type SMBVs of approximately 200 nm.

EXAMPLE 9

Preparation of a Fat Substitute: Attachment of Protein and Phospholipid Constituents of Milk to the Surface of Hydrophilic Matrices Prepared According to Example 4

100 g of hydrophilic matrices prepared according to Example 4 are placed in a 3 liter mixer. 10 g of protein and phospholipid constituents are added.

1 liter of water is introduced progressively and with stirring.

The whole mixture is homogenized at a rate of 80 l/h and at 200 bars (Westfalia homogenizer).

A creamy preparation is obtained which contains hardly any free protein and phospholipid constituents: two controls are carried out with protein and phospholipid constituents alone. A control (No. 1) and the preparation are centrifuged. The level of proteins is measured, by the Bradford method, in the uncentrifuged control, in the supernatant of the centrifuged control and in the supernatant of the preparation. Analyses are carried out on 100 ml. 0.5 g of proteins is measured in the supernatant of the centrifuged control and 0.05 g is measured in the supernatant of the preparation. From these results, the amount of proteins present in the centrifugate of the control No. 1 is deduced, i.e. 0.05 g, and, consequently, the amount of proteins anchored to the hydrophilic matrices, i.e. 0.4 g.

The percentage of proteins attached is 80% with respect to the amount of proteins initially introduced.

Moreover, the centrifugate of the preparation is dried and then washed, by filtration with chloroform, so as to extract the phospholipids. The chloroform is then evaporated and the remaining phospholipids are weighed. The measurement gives 0.4 g, i.e. 80% with respect to the amount of phospholipid constituents initially introduced.

EXAMPLE 10

Incorporation of an Enzyme, Glucose Oxidase (GO), in L-Type SMBVs

Glucose oxidase (GO) is an acidic protein having an isoelectric point of 3.5 and an average molecular weight of 180,000 daltons. 0.3 grams of QAE-type cores, obtained according to Example 2 and then 5, and 0.6 grams of GO are mixed, in the dry state. The mixture is then progressively hydrated by addition of 1.5 milliliters of buffer at pH 7, above the pI of GO, with stirring at room temperature, and then left stirred overnight in a refrigerator (4° C.). The pH is then adjusted to 3, below the pI of GO, and incubated for an additional 30 min. The preparation is then dispersed in 48.5 milliliters of distilled water, the pH adjusted to 7 and lyophilized in the presence of ammonium bicarbonate. The cores charged with GO thus obtained are mixed with 0.15 grams of powdered hydrogenated soya phosphatidylcholine (Nattermann, Fr.). The mixture is hydrated with 150 milliliters of distilled water and homogenized in a Rannie Mini Lab 12-51 homogenizer (APV Rannie, Copenhagen, DK) under a pressure of 300 bars. L-type SMBVs charged with GO are thus obtained, with an encapsulation yield of 92% and a degree of incorporation of 184% with respect to the weight of the cores, quantitatively determined by UV at 278 nm after ultrafiltration of the suspension.

EXAMPLE 11

Incorporation of an Enzyme, Lactoperoxidase (LP), in PS-Type SMBVs

Lactoperoxidase (LP) is an antibacterial enzyme. It is a basic protein having an isoelectric point of 9.6 and an average molecular weight of approximately 80,000 daltons.

0.5 gram of anionic (CM) PS-type SMBVs, obtained according to Example 3 and then 5, is suspended in 100 milliliters of a buffer adjusted to pH 7, below the pI of LP, in a 250 ml round-bottomed flask. 0.5 g of LP (BioSerae), dissolved in 1 milliliter of water, is then introduced with stirring.

The mixture is stirred overnight in a refrigerator (4° C.). The pH is then adjusted to 9.8, above the pI of LP, and incubated for 30 min. The pH is then brought back to 7 and the suspension is then lyophilized in the presence of ammonium bicarbonate (20 grams/liter). PS-type SMBVs charged with LP are obtained with a charging yield of 99% and a degree of incorporation of 99% with respect to the weight of the cores, from quantitative determination by UV at 412 nm.

EXAMPLE 12

Antibacterial Activity of the LP Encapsulated in PS-Type SNBVs and go Encapsulated in L-Type SNBVs Mixture

* In vitro quantitative determination of the activity:

1 ml of a 1M glucose solution, 0.2 ml of an ortho-phenylenediamine solution (1 mg/ml in a citrate buffer, pH 5.6, concentration 10 mM) and 1.6 ml of a citrate buffer solution (10 mM, pH 5.6) are mixed.

Moreover, 0.2 mg of PS-type SMBVs containing lactoperoxidase, prepared according to Example 11, and 1.8 mg of L-type SMBVs containing glucose oxidase, prepared according to Example 10, are mixed in 1 ml of water.

0.2 ml of this suspension is added to the 2.8 ml prepared above and stirring is carried out for 2 minutes at room temperature.

The colored reaction which develops is stopped with 1 ml of 2N sulfuric acid and the coloration is read at 490 nm against a blank which does not contain SMBV.

The presence of an intense coloration shows that the two enzymes encapsulated in the L-type SMBVs retain their activity. Quantitative determination of the activity of the encapsulated enzymes gives a result comparable with that obtained with the enzymes in aqueous solution at the same concentration.

* Antibacterial activity against a strain of *Escherichia coli:*

An LB glucose culture medium, mixed with a gelose agar, is prepared and poured into antibiogram dishes. The strain of *E. coli* is inoculated at the surface of the gelose at the rate of 200 µl/dish. Sterile paper disks are impregnated with suspensions of encapsulated or non-encapsulated enzymes and deposited on the gelose of the inoculated dishes. The dishes are left to incubate for 24 h at 37° C. and the inhibition diameters around the disks are measured.

The disks were impregnated with enzyme concentrations varying from 0.05 to 0.6 mg/ml of LP and from 0.8 to 10 mg/ml of GO. The inhibition diameters vary from 12 to 20 mm and are comparable, whether or not the enzymes have been encapsulated.

EXAMPLE 13

Stabilization of the Antibacterial Activity of Enzymes Encapsulated in SMBVs Three batches of glucose oxidase were prepared. Batch 1 is composed of a 0.2 mg/ml aqueous GO solution, batch 2 of an aqueous GO suspension encapsulated in SMBVs prepared according to the above patents, with a degree of encapsulation of 200% with respect to the weight of particles and in which the GO concentration is 0.2 mg/ml, and batch 3 of an aqueous GO suspension encapsulated in L-type SMBVs according to Example 10 and in which the GO concentration is also 0.2 mg/ml.

These three suspensions are left at 4° C. and quantitatively determined every week and then every month by the method described in Example 12. The activity of the GO solution decreases with time and becomes zero after 250 days. In contrast, the activity of the two suspensions of GO encapsulated either in SMEVs or in L-type SMBVs stays constant and remains equal to 100% of the initial activity after 320 days.

Moreover, a 0.1 mg/ml aqueous lactoperoxidase solution and a suspension of LP encapsulated in PS-type SMBVs prepared according to Example 11 and in which the LP concentration is also 0.1 mg/ml are also prepared.

These two suspensions are left at 4° C. and quantitatively determined every week and then every month by the method described in Example 12. The activity of the LP solution decreases with time and, after 90 days, the residual activity is no more than 35% of that of the initial activity. In contrast, the activity of the suspension of LP encapsulated in PS-type SMBVs stays constant and remains equal to 100% of the initial activity after 90 days.

EXAMPLE 14

Incorporation of Procyanidol Oligomers (PCOs) in L-Type or Complete SMBVs

A—Incorporation of PCOs in a gel of quaternary ammonium type

Procyanidol oligomers (PCOs) are antioxidizing agents of the hydrolyzable tannin family (flavonoids). They have properties for combating free radicals. Their average molecular weight is approximately 2000 daltons. They are soluble in water at a pH below 7.

5 grams of PCOs are dissolved in a minimum amount of distilled water (approximately 5 milliliters) and 10 grams of gel of quaternary ammonium type, prepared according to Example 2, are introduced. The mixture is hydrated with 180 milliliters of buffer at pH 6, above the mean pKa of PCOs, with stirring, in order to obtain a homogeneous paste. The mixture is left stirred overnight. The pH is then brought to 3.5, below the mean pKa of PCOs, left to incubate for 30 min, with stirring, and then washed with distilled water by centrifuging in order to remove the free PCOs. The amount of free PCOs in the supernatant is quantitatively determined by UV at 280 nm. An encapsulation yield of 82% and a degree of charging of 41% with respect to the weight of the gel are obtained.

This charged gel is then dispersed in 500 milliliters of distilled water and homogenized in a Rannie Mini Lab 12-51 homogenizer (APV Rannie, Copenhagen, DK) under a pressure of 600 bars for 15 minutes at a flow rate of 10 liters/hour. A suspension of PS-type SMBVs charged with PCOs with a size centered around 200 nm is obtained.

B—Production of L-type SMBVs of 200 nm charged with PCOs

The PS-type SMBVs suspension obtained above is placed in a Rannie Mini Lab 12-51 homogenizer under a pressure of 300 bars.

0.5 grams of hydrogenated soya phosphatidylcholine (Nattermann, Fr.) is then injected directly into the suspension which is recirculating in the homogenizer, under a pressure of 300 bars, and homogenization is carried out for 12 minutes with a flow rate of 10 liter/hour. The suspension obtained contains dispersed particles of approximately 200 nm.

C—Production of "complete" SMBVs of 200 nm charged with PCOs:

"Complete" SMBVs are prepared as described above by means of PS-type SMBVs charged with PCOs by drying (lyophilization), regioselective acylation in an organic solvent and formation of an external phospholipid lamella.

D—Stabilization of procyanidol oligomers (PCOs) in L-type SMBVs

An emulsion of oil-in-water type is prepared and divided into three batches. PCOs are incorporated in the first batch at the final concentration of 0.05%. PCOs encapsulated in L-type SMBVs are incorporated in a second batch and PCOs encapsulated in "complete" SMBVs are incorporated in the third batch. The final concentration of these last two batches in PCOs is also 0.05%. These three emulsions have a homogeneous creamy-white color.

A sample of each of the three batches is placed under a UV lamp (254 nm) for 48 hours and then left with the light excluded. After 10 days, the emulsion containing the free PCOs has a very intense brown coloration, the emulsion containing PCOs encapsulated in L-type SMBVs has a slightly stronger creamy-white coloration whereas the emulsion containing PCOs encapsulated in "complete" SMBVs has not changed.

In the same way, the stability of the PCOs in these emulsions is tested over 6 months at 40° C. The cream containing the PCOs encapsulated in "complete" SMBVs has not changed significantly in coloration, that containing the PCOs encapsulated in L-type SMBVs has a slightly more intense color whereas that containing free PCOs has become brownish.

EXAMPLE 15

Incorporation of an Anticancer Antibiotic, Doxorubicin, in L-Type SABVs by Using the Method of Charging by Topological Control Doxorubicin is an anticancer antibiotic belonging to the anthracycline family. It is an amphiphilic product characterized by a polyaromatic aglycone, conferring characteristic fluorescence properties on the molecule, and by an amino sugar, daunosamine. The molecular weight of the hydrochloride is 580 and its pKa is 8.5.

Polysaccharide cores prepared as above are used.

1—Incorporation of doxorubicin without topological control

Doxorubicin (0.1 g) in aqueous solution is added progressively to the polysaccharide cores (0.5 g) with magnetic stirring. The suspension obtained is then left stirring for 17 h at room temperature and with the light excluded.

The polysaccharide cores thus charged with doxorubicin have completely precipitated. Even in the presence of detergent and of phospholipids, they cannot be correctly dispersed with a size of 20 nm.

The incorporation of doxorubicin without topological control leads to a complete aggregation of the polysaccharide cores and cannot be used for forming L-type SMBVs of 20 nm.

2—Incorporation of doxorubicin with topological control

Doxorubicin (0.1 g) in aqueous solution is added progressively to the polysaccharide cores (0.5 g) with magnetic stirring. The pH is adjusted to 7, below the pKa of doxorubicin, during the addition. The suspension obtained is stirred for 17 h at room temperature and with the light excluded. The pH is then adjusted to 9, above the pKa of doxorubicin, and incubated for 30 min. The suspension of polysaccharide cores is then divided in two: one part is analyzed as polysaccharide cores and the other part of the polysaccharide cores is prepared as L-type SMBVs.

a—PS-type SMBVs

After the incubation step at pH 9, the suspension obtained is diluted in 1 l of water and brought to pH 7. The cores thus charged are analyzed: filtration through 0.2 $\mu$m of the suspension exhibits a yield of doxorubicin of greater than 95%, which indicates that the size of the polysaccharide cores is 20 rim, and centrifugal ultrafiltration of an aliquot of the suspension demonstrates the absence of free doxorubicin. The results indicate the presence of 4 mg of doxorubicin in the ultrafiltrate and of 46 mg of doxorubicin in the polysaccharide cores, which corresponds to a yield of 92% and a degree of encapsulation of 18% of doxorubicin. Filtration through 0.2 $\mu$m of the suspension obtained exhibits a yield of greater than 95%, which indicates that the size of the SMBVs is 20 nm.

a L—type SMBVs

The polysaccharide cores are then dispersed with the phospholipids (0.25 g) (80/20 by weight EYPC/cholesterol) which have been predispersed in 50 mM hecameg, at a concentration of 10 g/l. The suspension obtained is suddenly diluted in 1 l of water. The detergent is then removed by ultrafiltration. The doxorubicin is then quantitatively determined in the ultrafiltrate and in the SMBVs obtained. The results indicate the presence of 2.5 mg of doxorubicin in the ultrafiltrate and of 47.5 mg of doxorubicin in the SMBVs, which corresponds to a doxorubicin yield of 95% and a degree of encapsulation of doxorubicin of 19% with respect to the polysaccharide cores. Filtration through 0.2 $\mu$m of the suspension obtained exhibits a yield of greater than 95%, which indicates that the size of the SMBVs is 20 nm.

EXAMPLE 16

Postcharging of Doxorubicin in Polysaccharide Cores

Doxorubicin is an anticancer antibiotic belonging to the anthracycline family. It is an amphiphilic product characterized by a polyaromatic aglycone, conferring characteristic fluorescence properties on the molecule, and by an amino sugar, daunosamine. The molecular weight of the hydrochloride is 580 and its $pK_a$ is 8.2–8.5.

* Incorporation of doxorubicin in polysaccharide cores

The polysaccharide cores used were crosslinked and functionalized by $POCl_3$ and have a size of 20 nm. Their ionic density is 1.59 mequiv P04/g.

The polysaccharide cores (10 mg) are dispersed in water (10 ml) under ultrasound. The pH of the cores suspension is adjusted to 7 with 0.1N NaOH. The doxorubicin (4.6 mg), as a 5 mg/ml solution in water, is slowly added while sonicating in 20 μl portions. The pH is adjusted to 7, if necessary, with 0.1N NaOH.

The polysaccharide cores thus charged are characterized by:

their ability to be filtered through 0.2 μm: the filtration yield is determined by the ratio of the concentrations before and after filtration. After incorporation, 100 μl of the suspension of charged polysaccharide cores are withdrawn in order to determine the doxorubicin concentration. The remainder of the suspension is filtered through a membrane with a porosity of 0.2 μm. A 100 μl aliquot is again withdrawn for the quantitative determination of the doxorubicin. The doxorubicin is quantitatively determined by HPLC after release of the polysaccharide cores.

$$\text{Filtration yield through } 0.2\,\mu m\ (\%) = \frac{\text{doxorubicin concentration after filtration}}{\text{doxorubicin concentration before filtration}} \times 100$$

the nonincorporated fraction which is determined by centrifugal ultrafiltration. After filtration, 1 ml of the suspension of polysaccharide cores, diluted to ½, is deposited on the centrifugal ultrafiltration system (Microsep) and then centrifuged at 7500 g for 30 min. The ultrafiltrate obtained is quantitatively determined by HPLC for doxorubicin.

$$\text{Nonincorporated fraction } (\%) = \frac{\text{doxorubicin concentration in the ultrafiltrate}}{\text{doxorubicin concentration after filtration}} \times 100$$

The filtration yield is 97% and the nonincorporated fraction is less than 5%, leading to an incorporation yield of 99%.

* Comparison of the behavior under physiological conditions of doxorubicin incorporated in polysaccharide cores and in SMBVs The particles which are postcharged in doxorubicin, polysaccharide cores or SMBVs, are incubated in PBS at 37° C. at a doxorubicin concentration of 50 μg/ml. At time 0 h and 4 h, 1 ml of the particle suspension is withdrawn and ultrafiltered by centrifuging (7500 g, 30 min) on a Microsep in order to determine the doxorubicin fraction released. The ultrafiltrate obtained is then quantitatively determined for doxorubicin by HPLC. The results are presented in the following table:

| % of doxorubicin remaining incorporated | Type of particles PSN | Type of particles SMBV |
|---|---|---|
| time 0 h | 67 +/− 1 | 62 +/− 1 |
| time 4 h | 64 +/− 3 | 55 +/− 5 |

Behavior under physiological conditions of polysaccharide cores and of SMBVs which have incorporated doxorubicin by postcharging The results obtained indicate a difference in behavior of doxorubicin incorporated in these two types of particles: doxorubicin remains incorporated more strongly in the polysaccharide cores than in the SMBVs.

EXAMPLE 17

POSTCRARGING OF DOXORUBICIN IN SMBVs

* Incorporation of doxorubicin in SNBVs (of L-type or not)

The SMBVs are prepared from acylated cores on which the phospholipid lamella (100% by weight) is formed by the detergent method.

Briefly, the phospholipids (10 mg), with the composition 80/20 EYPC/cholesterol (by weight), are dispersed in 50 nM hecameg (2 ml). The acylated cores (10 mg) are added to the phospholipids and then subjected to an ultrasonic bath for 5 min. The suspension obtained is diluted in 8 ml of distilled water under the CMC of the hecameg, which is 20 nM, and then dialyzed extensively. The SMBVs obtained are filtered through 0.2 μm and stored under sterile conditions.

The L-type SMBVs are prepared according to the same protocol but by using polysaccharide cores in place of the acylated cores.

The pH of the SMBV (20 mg) suspension is adjusted to 7 with 0.1N NaOH. The doxorubicin (4.6 mg), as a 5 mg/ml solution in water, is added slowly while sonicating in 20 μl portions. The pH is adjusted to 7, if necessary, with 0.1N NaOH.

The SMBVs thus charged are characterized by:

their ability to be filtered through 0.2 μm: the filtration yield is determined by the ratio of the concentrations before and after filtration. After incorporation, 100 μl of the suspension of charged SMBVs are withdrawn in order to determine the doxorubicin concentration. The remainder of the suspension is filtered through a membrane with a porosity of 0.2 μm. A 100 μl aliquot is again withdrawn for the quantitative determination of the doxorubicin. The doxorubicin is quantitatively determined by HPLC after release of the polysaccharide cores.

$$\text{Filtration yield through } 0.2\,\mu m\ (\%) = \frac{\text{doxorubicin concentration after filtration}}{\text{doxorubicin concentration before filtration}} \times 100$$

the nonincorporated fraction which is determined by centrifugal ultrafiltration. After filtration, 1 ml of the suspension of SMBVs, diluted to ½, is deposited on the centrifugal ultra-filtration system (Microsep) and then centrifuged at 7500 g for 30 min. The ultrafiltrate obtained is quantitatively determined by HPLC for doxorubicin.

$$\text{Nonincorporated fraction (\%)} = \frac{\text{doxorubicin concentration in the ultrafiltrate}}{\text{doxorubicin concentration after filtration}} \times 100$$

The filtration yield is 95% and the nonincorporated fraction is less than 5%, leading to an incorporation yield of 99%.

* Behavior under physiological conditions of doxorubicin incorporated in L-type SMBVs The particles which have been postcharged with doxorubicine SMBVs of L-type or not, are incubated in PBS at 37° C. at a doxorubicin concentration of 50 μg/ml. At time 0 h and 4 h, 1 ml of the particle suspension is withdrawn and ultrafiltered by centrifuging (7500 g, 30 min) on a Microsep in order to determine the doxorubicin fraction released. The ultrafiltrate obtained is then quantitatively determined for doxorubicin by HPLC.

The results are presented in the following table:

| % of doxorubicin remaining incorporated | L-type SMBVs | SMBV |
|---|---|---|
| time 0 h | 58 +/− 1 | 62 +/− 1 |
| time 4 h | 54 +/− 3 | 55 +/− 5 |

Behavior under physiological conditions of SMBVs, of L-type or not, which have incorporated doxorubicin by postcharging The results obtained indicate that L-type SMBVs which are charged with doxorubicin have a behavior under physiological conditions which is similar to that of SMBVs.

Legend of FIG. 1:
- □ 4° C.
- ♦ 37° C.
- □ 100° C.

Figure 2:
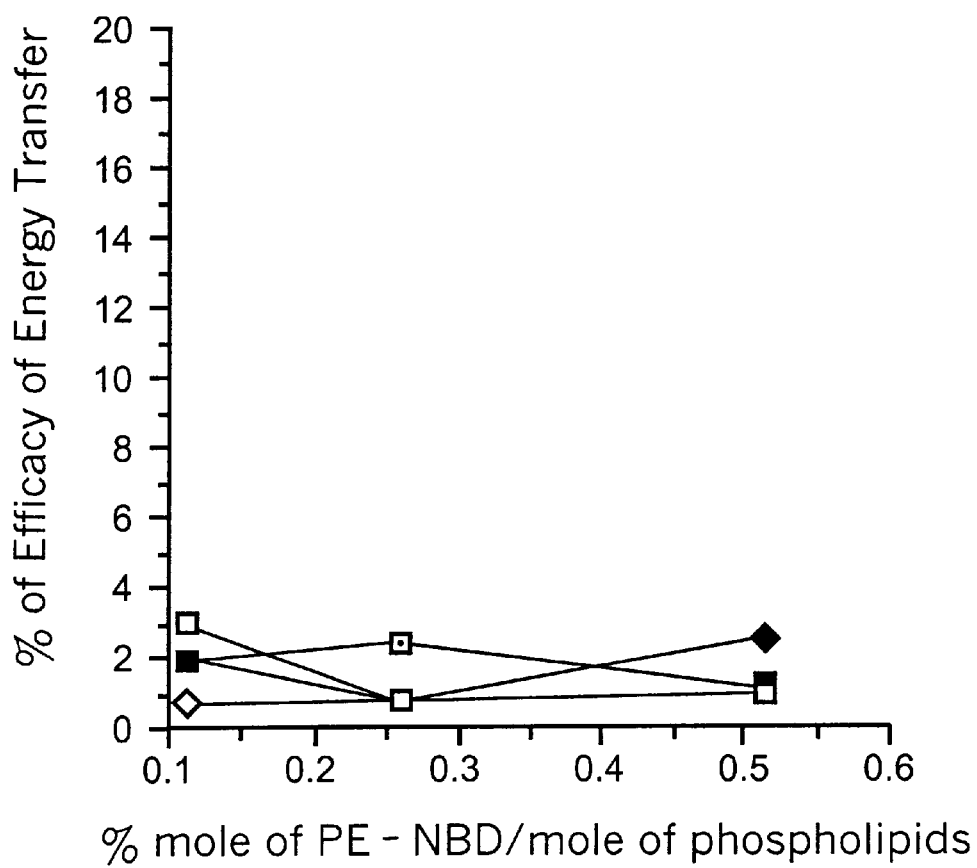
FIG. 2 Energy transfer between PS-type SMBVs labeled using rhodamine and liposomes labeled using NBD.

Legend to FIG. 2:
- □ 4° C.
- ♦ 37° C.
- □ 100° C.
- ◇ 37° C. Ultrasound

Legend to FIG. 3:
- □ 4° C.
- ♦ 37° C.
- □ 100° C.

We claim:

1. A synthetic particulate vector, having a diameter of 10 nm to 5 μm comprising a non-liquid non active principle hydrophilic core, and an external layer which comprises amphiphilic compounds, wherein said external layer is combined with the core via hydrophobic interactions and/or ionic bonds.

2. The synthetic particulate vector according to claim 1, wherein the hydrophilic core comprises a matrix of polysaccharides or oligosaccharides which are naturally or chemically crosslinked.

3. The synthetic particulate vector according to claim 1, further comprising ionic ligands grafted onto the hydrophilic core.

4. The synthetic particulate vector according to claim 1, wherein the amphiphilic compounds of the external layer are selected from the group consisting of phospholipids, ceramides, ionic surface-active agents or nonionic surface-active agents.

5. The synthetic particulate vector according to claim 1, wherein the external layer further comprises at least one lipid compound selected from the group consisting of cholesterol, natural fatty acids and fat-soluble vitamins.

6. The synthetic particulate vector according to claim 1, further comprising an active principle in the core or in the external layer.

7. The synthetic particulate vector according to claim 1, wherein said vector has a diameter of between 20 and 200 nm.

8. The synthetic particulate vector according to claim 6, wherein said active principle is selected from the group consisting of antibiotics, antiviral agents, proteins, proteoglycans, peptides, polysaccharides, lipopolysaccharides, antibodies, antigens, insecticides, fungicides, compounds which act on the cardiovascular system, anticancer agents, antimalarial agents, antiasthmatic agents, compounds having an effect on the skin, and constituents of dairy fat globules.

9. A process for preparing a particulate vector according to claim 3 to 6, said process comprising:
    (a) encapsulating an acidic or basic ionizable active principle in a crosslinked hydrophilic matrix grafted by ligands of an ionic species of opposite ionic charge with that of the active principle, at a pH at which the active principle is in the ionized form;
    (b) varying the pH of the medium, with respect to the $pK_a$ of the active principle, to a value at which the active principle is not in an ionized form;
    (c) recovering the hydrophilic matrix which comprises the active principle; and
    (d) fixing a layer of amphiphilic compounds to the recovered matrix.

10. The process for preparing a particulate vector according to claim 9, comprising:
    (a) encapsulating a basic ionizable active principle in a crosslinked hydrophilic matrix grafted by acidic ionic ligands, at a pH below the $pK_a$ of the active principle; and
    (b) increasing the pH of the medium to a value above the $pK_a$ of the active principle.

11. The process for preparing a particulate vector according to claim 9, comprising:
    (a) encapsulating an acidic ionizable active principle in a crosslinked hydrophilic matrix grafted by basic ionic ligands, at a pH above the $pK_a$ of the active principle; and
    (b) decreasing the pH of the medium to a value below the $pK_a$ of the active principle.

12. The process for preparing a particulate vector according to claim 9, wherein the hydrophilic matrix comprises polysaccharides or oligosaccharides which are naturally or chemically crosslinked.

13. A pharmaceutical composition of matter comprising a particulate vector according to claim 1, and a pharmaceutically acceptable support for administration thereof.

14. A cosmetological composition comprising a particulate vector according to claim 1, and cosmetologically acceptable excipients therefor.

15. A food composition comprising a particulate vector according to claim 1.

16. A process for preparing a pharmaceutical composition comprising encapsulating an acidic or basic ionizable active principle in a particulate vector according to claim 1.

17. A method of treating a medical condition comprising administering a vector according to claim 1 to a patient in need of such treatment.

* * * * *